US012594066B2

(12) United States Patent
Shaligram et al.

(10) Patent No.: US 12,594,066 B2
(45) Date of Patent: Apr. 7, 2026

(54) SURGICAL LIGATURE INSTRUMENT FOR MINIMALLY INVASIVE SURGERY

(71) Applicants: Abhijit Shaligram, Mountain House, CA (US); Ravi Mohanka, Mumbai (IN); Manish Mohanka, Coppell, TX (US); Gautam Gupta, Westford, MA (US)

(72) Inventors: Abhijit Shaligram, Mountain House, CA (US); Ravi Mohanka, Mumbai (IN); Manish Mohanka, Coppell, TX (US); Gautam Gupta, Westford, MA (US)

( * ) Notice: Subject to any disclaimer, the term of this patent is extended or adjusted under 35 U.S.C. 154(b) by 393 days.

(21) Appl. No.: 18/499,002

(22) Filed: Oct. 31, 2023

(65) Prior Publication Data

US 2024/0074746 A1     Mar. 7, 2024

Related U.S. Application Data

(63) Continuation-in-part of application No. 17/094,626, filed on Nov. 10, 2020, now Pat. No. 11,857,178.

(60) Provisional application No. 62/934,989, filed on Nov. 13, 2019.

(51) Int. Cl.
*A61B 17/04* (2006.01)
*A61B 17/00* (2006.01)

(52) U.S. Cl.
CPC ..................... *A61B 17/0467* (2013.01); *A61B 2017/00367* (2013.01); *A61B 2017/0042* (2013.01); *A61B 2017/00477* (2013.01); *A61B 2017/0474* (2013.01)

(58) Field of Classification Search
CPC ............ A61B 17/0467; A61B 17/0469; A61B 2017/0474; A61B 2017/0488
See application file for complete search history.

(56) References Cited

U.S. PATENT DOCUMENTS

| | | | |
|---|---|---|---|
| 1,822,330 A | 9/1931 | George | |
| 3,033,204 A | 5/1962 | Wood | |
| 3,090,386 A | 5/1963 | William | |
| 8,394,111 B2 * | 3/2013 | Yamamoto | A61B 17/0469 606/139 |
| 8,932,208 B2 | 1/2015 | Kendale et al. | |
| 2005/0143774 A1 | 6/2005 | Polo | |
| 2006/0200198 A1 | 9/2006 | Riskin et al. | |
| 2017/0296163 A1 | 10/2017 | Levin et al. | |
| 2018/0235604 A1 * | 8/2018 | Comee | A61B 17/0625 |

* cited by examiner

*Primary Examiner* — Sarah A Long
*Assistant Examiner* — Mohammed S Adam

(57)          ABSTRACT

The present invention is a surgical suturing device that assists in applying an open-looped, pre-knotted suture around a targeted area of application. The surgical suturing device contains a handle, a grasping mechanism, a clamp tube, a pusher tube, a cutter tube, and a pivot arm. A first coupler is positioned on the pivot arm. A second coupler is positioned at the end of the shaft, offset from the pivot arm. A suture knot is fitted over the second coupler, and a strand is connected to the first coupler. When activated, the pivot arm moves into a closed position, thereby encircling the suturing portion and joining the first coupler to the second coupler. Next, the suture knot is pushed forward off the second coupler and tightened up against the suturing portion. The pusher tube slides back, allowing the cutter tube to cut the excess suture cord.

20 Claims, 18 Drawing Sheets

SURGICAL LIGATURE INSTRUMENT FOR MINIMALLY INVASIVE SURGERY

FIELD OF THE INVENTION

The present invention relates generally to surgical suturing instrument. More specifically, the present invention is a surgical suturing instrument that allows a user to place an open-loop, pre-knotted suture over a targeted area of application without having to release hold over the targeted area of application.

BACKGROUND OF THE INVENTION

Currently, present society have enhanced current means of suturing during surgical procedures. In particular, traditional surgery can often involve looping a suture around a tissue and tying it off with knots. Clips can commonly be used to perform such function; however, they are mostly inflexible and inapplicable to most tissue types. Instead, pre-knotted sutures with a closed loop, known in the field as endoloops, can be favorable those applications unfulfilled by clips. However, these endoloops do present some challenges. For instance, in order to apply the endoloop to a target area of application, the user might have release and re-grasp their hold of the targeted area of application as they are trying to get the endoloop over or around the targeted area of application; sometimes repeatedly, which can unfavorable when dealing with certain targeted areas of application such as a bleeding vessel.

An objective of the present invention is to provide users with a device that is a surgical suturing instrument. The present invention intends to provide users with a device that can assist in applying an open-looped, pre-knotted suture around a targeted area of application, without the user having to release and re-grasp their hold on the targeted area of application repeatedly. The present invention intends to provide users with a device that utilizes an open-looped, pre-knotted suture that can be closed around a targeted area of application. The present invention intends to provide users with a device that can allow passage for said suture through to the front end of said device in which said suture is applied around targeted area of application. The present invention intends to provide users with a device that can grasp the free ends of said suture in order to form a closed loop around the targeted area of application. The present invention intends to provide users with a device that can allow passage of the knot of said suture through front tip of said device in order to close-off/tie-off said suture around targeted area of application.

SUMMARY OF THE INVENTION

The present invention is a surgical suturing device. The surgical suturing device comprises a handle, a grasping mechanism, a first jaw, a second jaw, a first coupler, and a second coupler. The first jaw and the second jaw each comprises a jaw body and a coupler receiver. The first coupler and the second coupler each comprises a strand receiver. The handle is operatively connected to the first jaw and the second jaw through the grasping mechanism. The coupler receiver is positioned adjacent to the jaw body, opposite to the grasping mechanism along the jaw body for each of the first jaw and the second jaw. In the preferred embodiment of the present invention, the coupler receiver mounts the first coupler and the second coupler to the first jaw and the second jaw. The first coupler is removably positioned within the coupler receiver of the first jaw. The strand receiver traverses into the first coupler and the second coupler. The second coupler is removably positioned within the coupler receiver of the second jaw.

In a second embodiment of the present invention, the surgical suturing device further comprises a clamp tube, a pusher tube, a cutter tube, and a pivot arm. The first coupler receiver is positioned adjacent to the pivot arm, while the second coupler receiver is positioned at the end of the shaft. A first strand of the suture cord is connected to the first coupler, while the suture knot is fitted over the second coupler. On the opposite end of the device, the clamp tube is connected to the trigger mechanism. When the user presses the trigger, the clamp tube moves the pivot arm into a closed position, thereby encircling the suturing portion and joining the first coupler to the second coupler. Next, the suture knot can be pushed forward and slide through the first coupler and through the first strand, thereby pushing the suture knot up to the suturing portion. This removes the excess slack in the suture cord. Once tightened, the user can then slide the pusher tube back to its original position while keeping the cutter tube in the extended position. In turn, the tip of the cutter tube is now exposed to the suture cord, allowing the user to cut the excess suture cord. The suture cord is then detached from the first coupler, allowing the user to safely remove the device away from the newly formed closed loop.

DETAIL DESCRIPTIONS OF THE INVENTION

Figure 1:
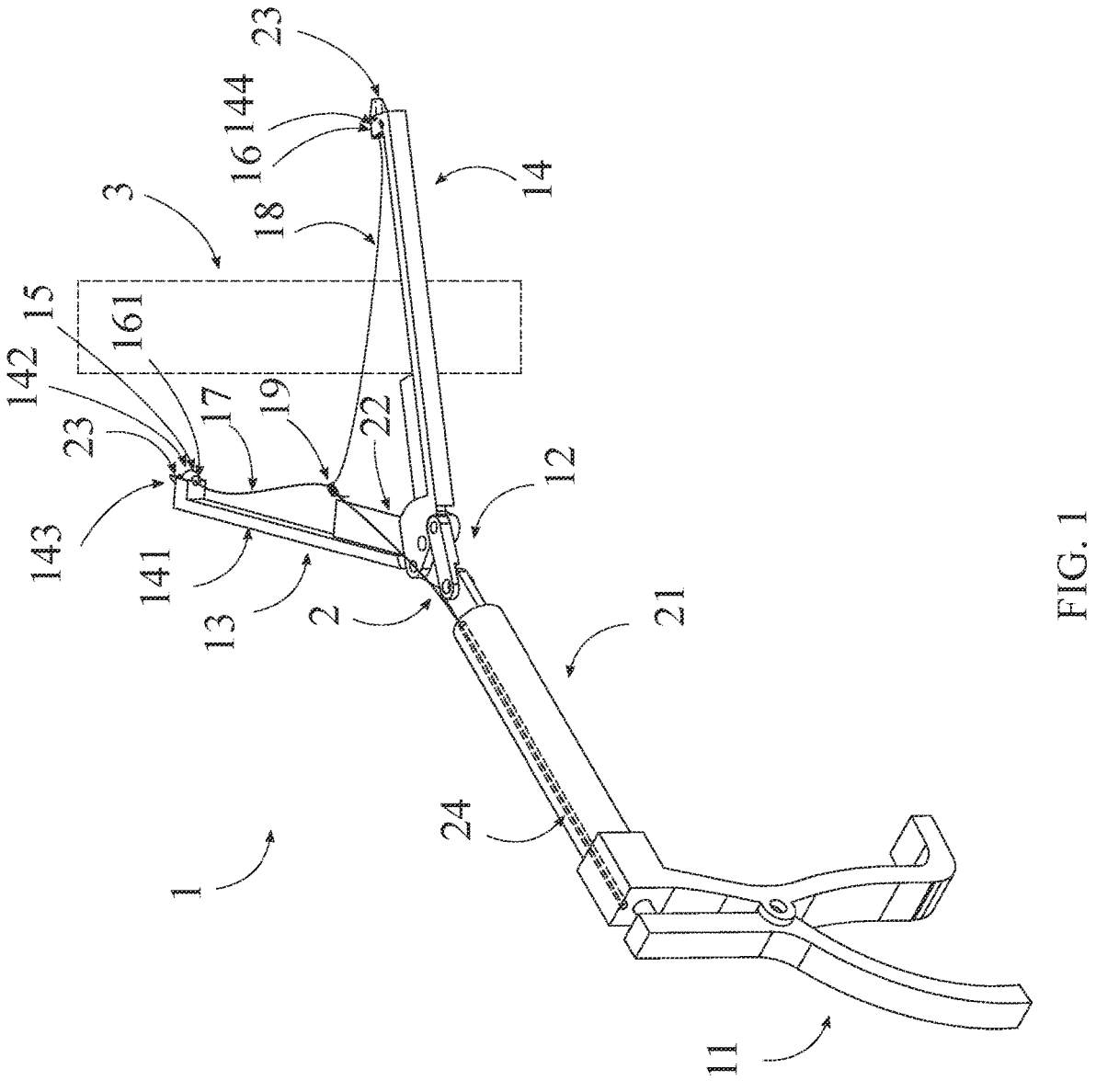
FIG. 1 is a perspective view of the present invention opened with an open loop.

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole. Hereinafter, each of the terms "forward" and "distal" refer to longitudinally outward, away from the user. Conversely, each of the terms "aft" and "proximal" refer to longitudinally inward, nearest the user.

In reference to FIGS. 1-6, the present invention is a surgical suturing device 1. The present invention can be of any shape, size, material, features, type or kind, orientation, location, quantity, components, and arrangements of components that would allow the present invention to fulfill the objectives and intents of the present invention. However, it can be preferred that the present invention be of a material that is sterile, hygienic, strong, durable, tough, light weight, easily cleanable, and/or easily manufacturable. The surgical suturing device 1 comprises a handle 11, a grasping mechanism 12, a first jaw 13, a second jaw 14, a first coupler 15, and a second coupler 16. The first jaw 13 and the second jaw 14 each comprises a jaw body 141 and a coupler receiver 142. The first coupler 15 and the second coupler 16 each comprises a strand receiver 161. The handle 11 is operatively connected to the first jaw 13 and the second jaw 14 through the grasping mechanism 12. The handle 11 can be of any shape, size, material, features, type or kind, orientation, location, quantity, components, and arrangements of components that would allow the present invention to fulfill the objectives and intents of the present invention. However, it can be preferred that the handle 11 assembly be of a material similar to and/or compatible with the material of the present invention. It can be preferred that the handle 11 assembly be of a general size that can accommodate the general sizes of an average user's hand. It can be preferred that the handle 11 be of a type or kind, shape, size, features, and/or components similar to handles commonly used or found on surgical devices. This can include, but is not limited to, the following: handles commonly found on laparoscopic suturing devices, laparoscopic grasper, ratcheting handle, or any other similarly related or similarly styled handle 11.

Figure 3:
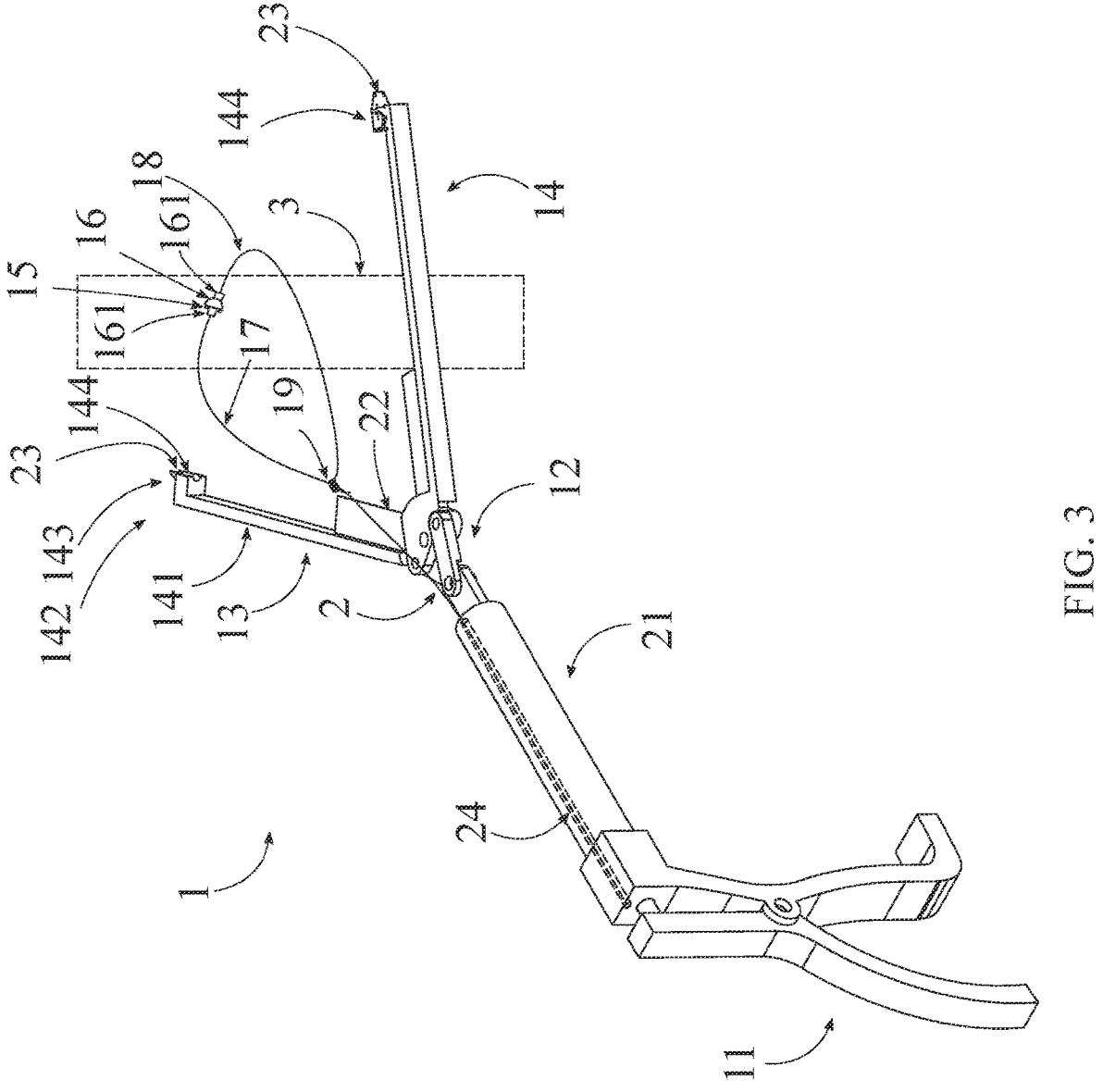
FIG. 3 is a perspective view of the present invention opened with the closed loop wrapped around a suturing portion.
Figure 5:
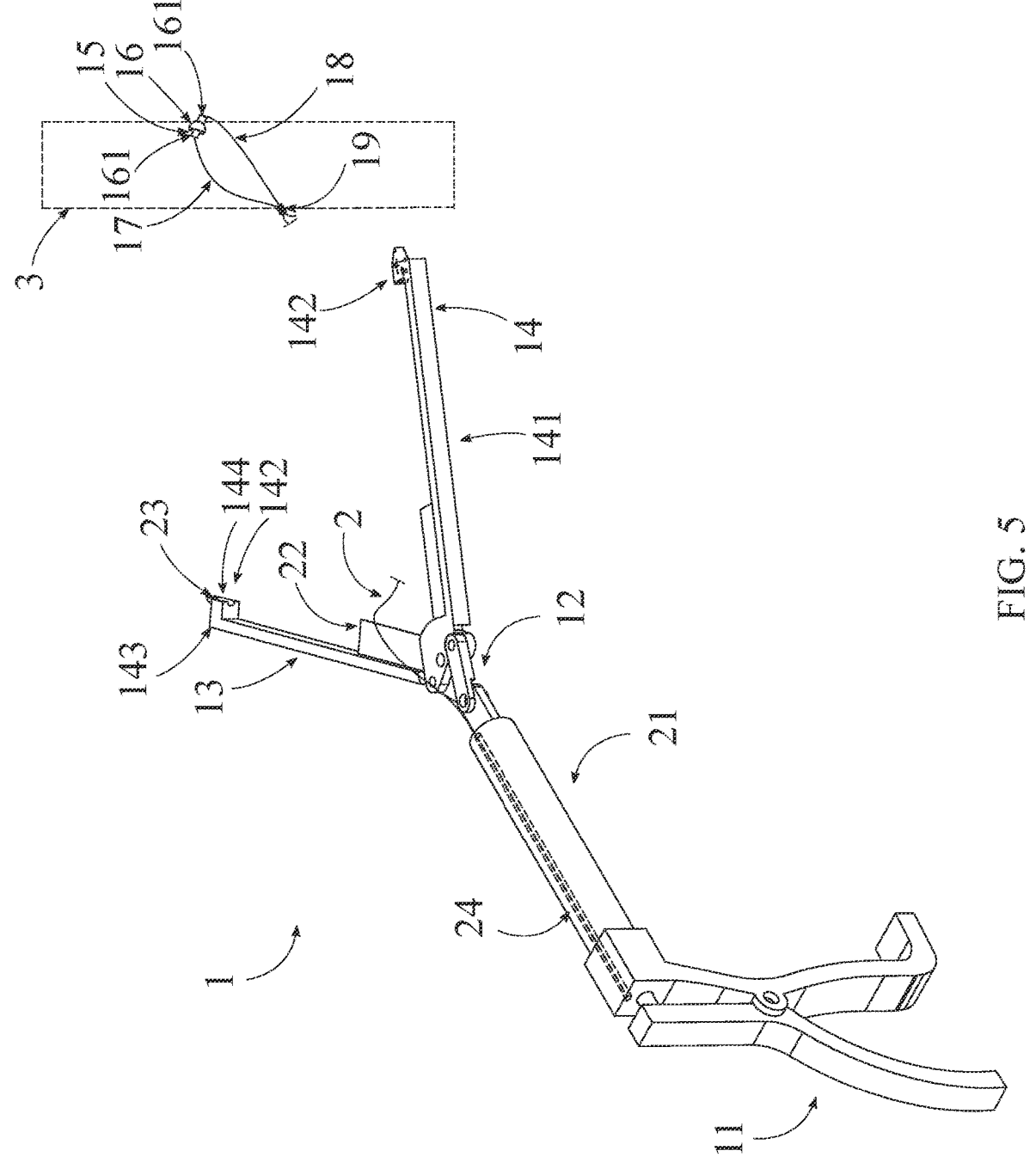
FIG. 5 is a perspective view of the present invention opened with a suture cord being cut along the tightened closed loop.

In reference to FIGS. 1, 3, and 5, the coupler receiver 142 is positioned adjacent to the jaw body 141, opposite to the grasping mechanism 12 along the jaw body 141 for each of the first jaw 13 and the second jaw 14. In the preferred embodiment of the present invention, the coupler receiver 142 mounts the first coupler 15 and the second coupler 16 to the first jaw 13 and the second jaw 14. The first coupler 15 is removably positioned within the coupler receiver 142 of the first jaw 13. The strand receiver 161 traverses into the first coupler 15 and the second coupler 16. The second coupler 16 is removably positioned within the coupler receiver 142 of the second jaw 14.

Figure 2:
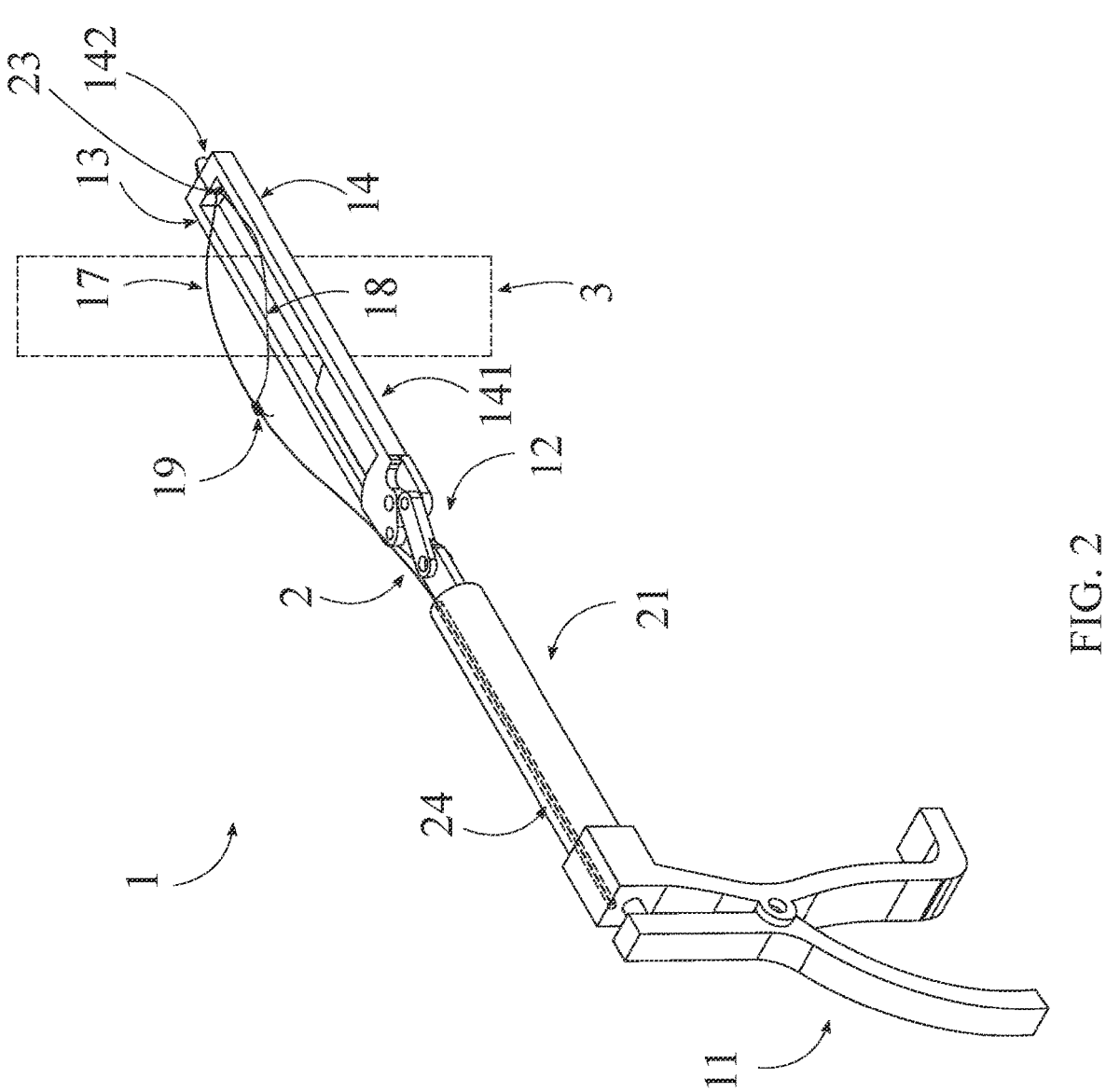
FIG. 2 is a perspective view of the present invention closed with a closed loop.

The surgical suturing device 1 further comprises a first strand 17 and a second strand 18. The first strand 17 is connected to the strand receiver 161 of the first coupler 15. The second strand 18 is connected to the strand receiver 161 of the second coupler 16. The first strand 17 serves as one segment of a suture cord 2 that will form the loop in conjunction with the second strand 18 which serves as the other segment of the suture cord 2. The surgical suturing device 1 further comprises an adjustment element 19. The adjustment element 19 is operatively connected to the first strand 17 and the second strand 18. In the preferred embodiment of the present invention, the adjustment element 19 may take the form of any suitable adjustment element 19 such as, but not limited to suture knots, clips, or any other suitable adjustment element 19 used to tighten the formed loop along a suturing portion 3. In the preferred embodiment of the present invention, the first coupler 15 and the second coupler 16 conjoin the first strand 17 and the second strand 18 together, while disengaging along the jaw body 141, forming a completed suture loop, as shown in FIGS. 2 and 3.

The surgical suturing device 1 further comprises a shaft 21, as shown in FIGS. 1-6. The handle 11 is connected adjacent to the shaft 21. The grasping mechanism 12 traverses along the shaft 21 between the handle 11 and the first jaw 13 and the second jaw 14. The shaft 21 can be of any shape, size, material, features, type or kind, orientation, location, quantity, components, and arrangements of components that would allow the present invention to fulfill the objectives and intents of the present invention. However, it can be preferred that the shaft 21 be of a material similar to and/or compatible with the material of the handle 11. It can be preferred that the shaft 21 be of a shape similar to a cylindrical-like shaped figure. It can be preferred that the shaft 21 be located at the front face of the handle 11 assembly and near to the top face of the handle 11 assembly.

The surgical suturing device 1 further comprises a cutter 22, as shown in FIGS. 1, 3, and 5. The cutter 22 is positioned adjacent to the jaw body 141 of the first jaw 13 and the second jaw 14, opposite to the strand receiver 161. The cutter 22 can be of any shape, size, material, features, type or kind, orientation, location, quantity, components, and arrangements of components that would allow the present invention to fulfill the objectives and intents of the present invention. The cutter 22 allows the user to cut the excess suture cord 2 once the suture has been applied to the suturing area, as shown in FIG. 5. The surgical suturing device 1 further comprises a strand aperture 23, as shown in FIGS.

Figure 4:
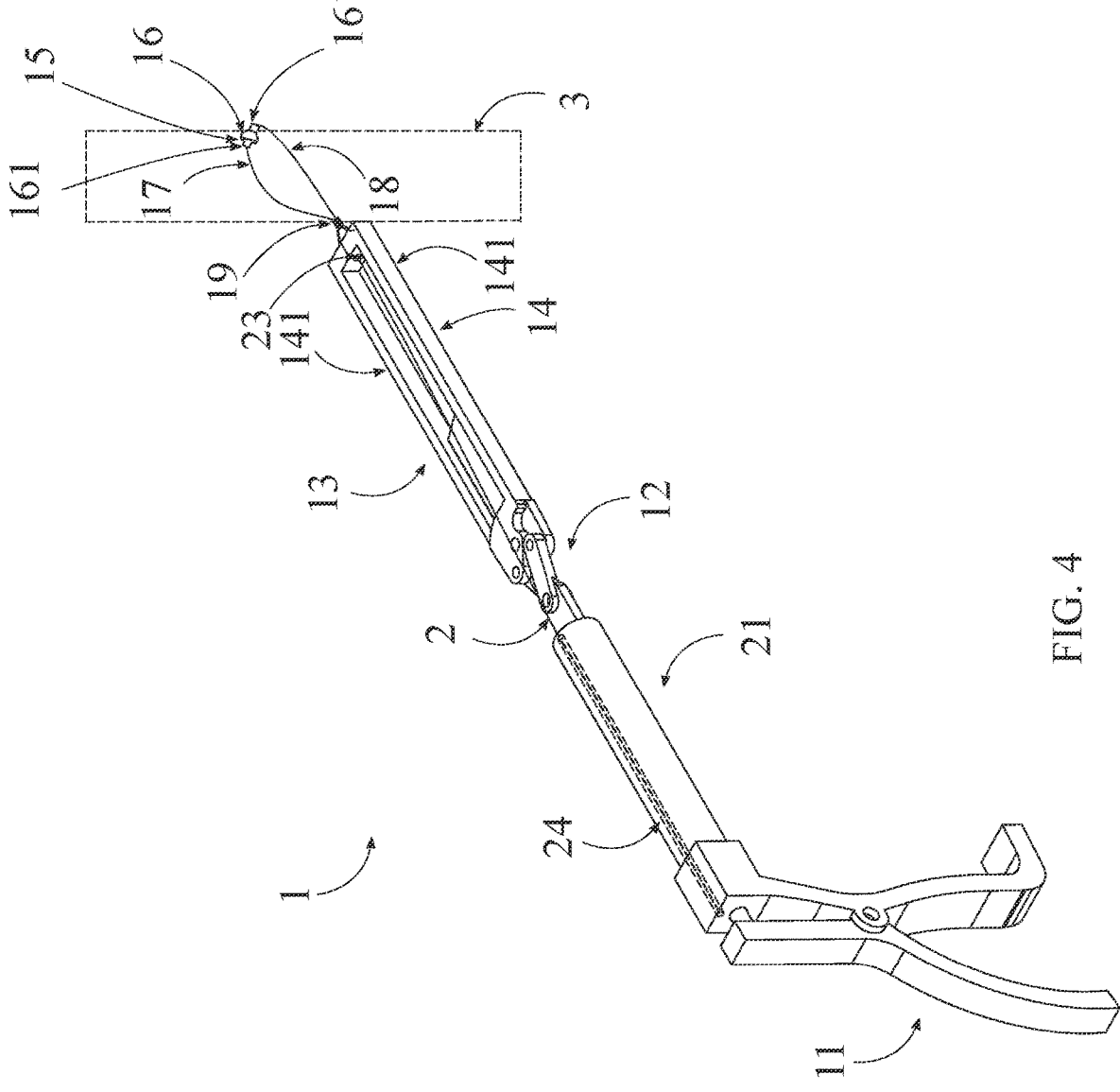
FIG. 4 is a perspective view of the present invention closed with the closed loop being tightened along the suturing positioned.

1-5. The strand aperture 23 traverses through the coupler receiver 142. The strand aperture 23 allows the user to handle 11 the suture cord 2 when tightening the loop along the suturing portion 3, as shown in FIG. 4.

Figure 6:
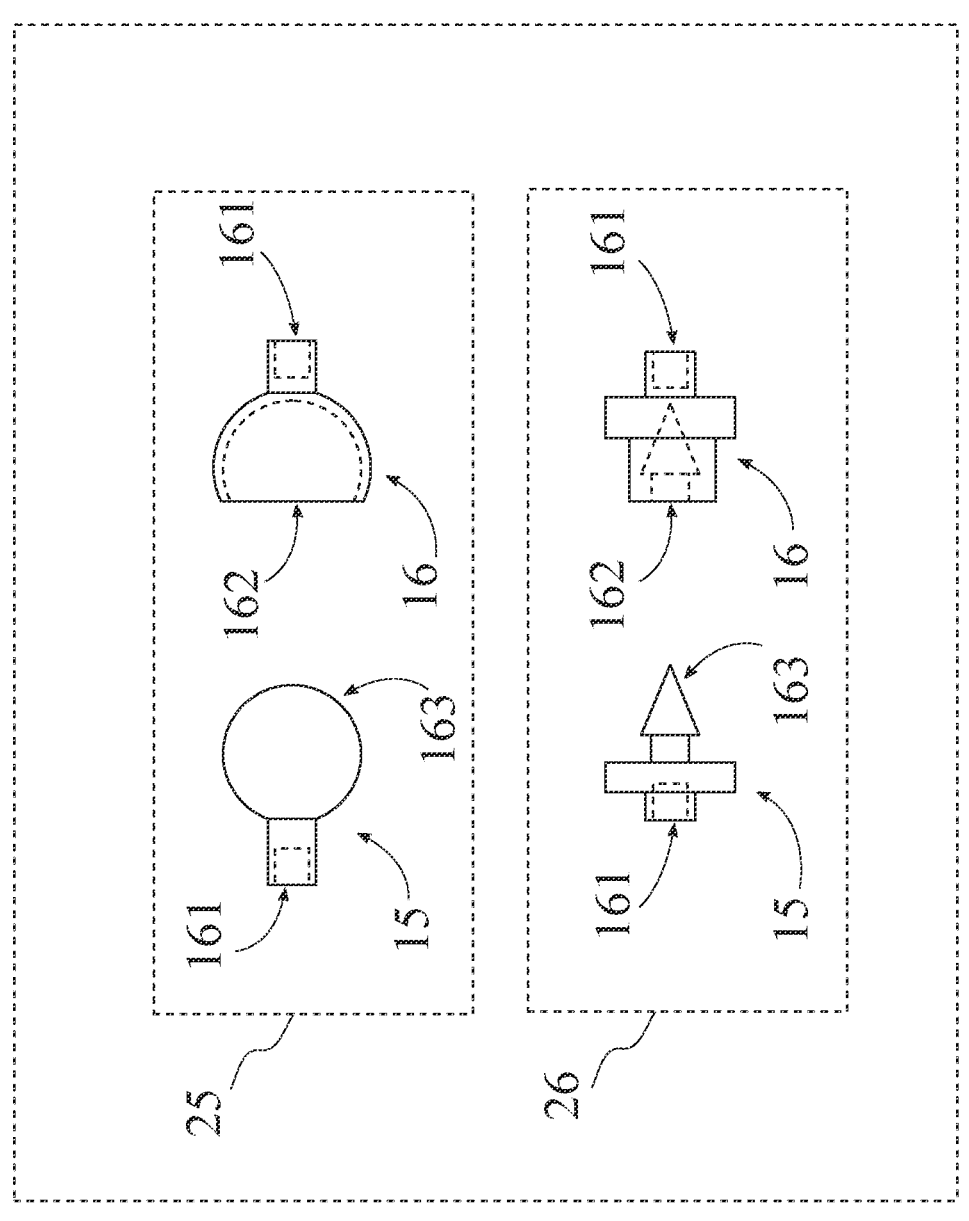
FIG. 6 is a diagram view of a ball and socket coupler and a snap rivet coupler.
Figure 7:
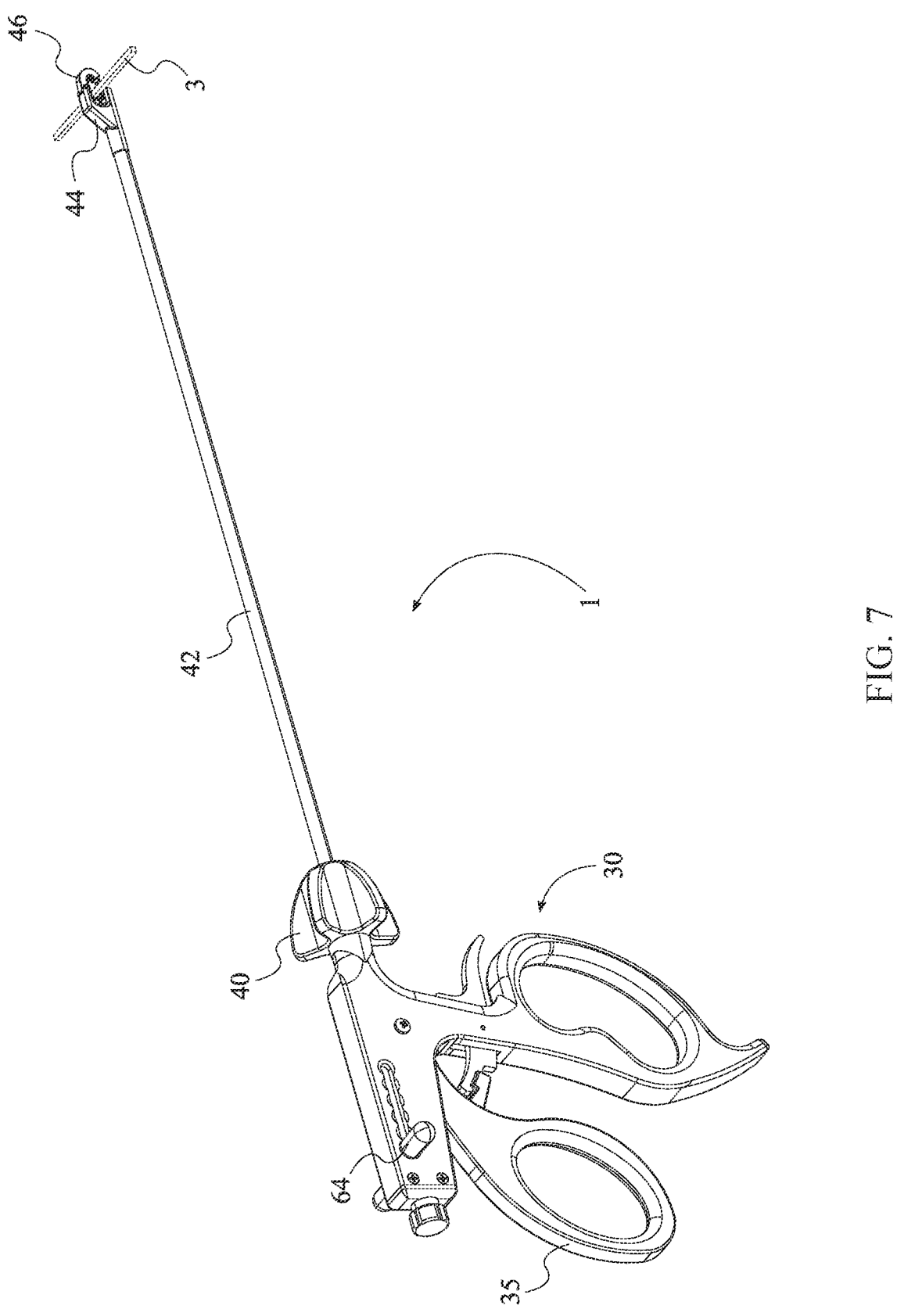
FIG. 7 is a rear perspective view of the present invention, in accordance with another embodiment.
Figure 8:
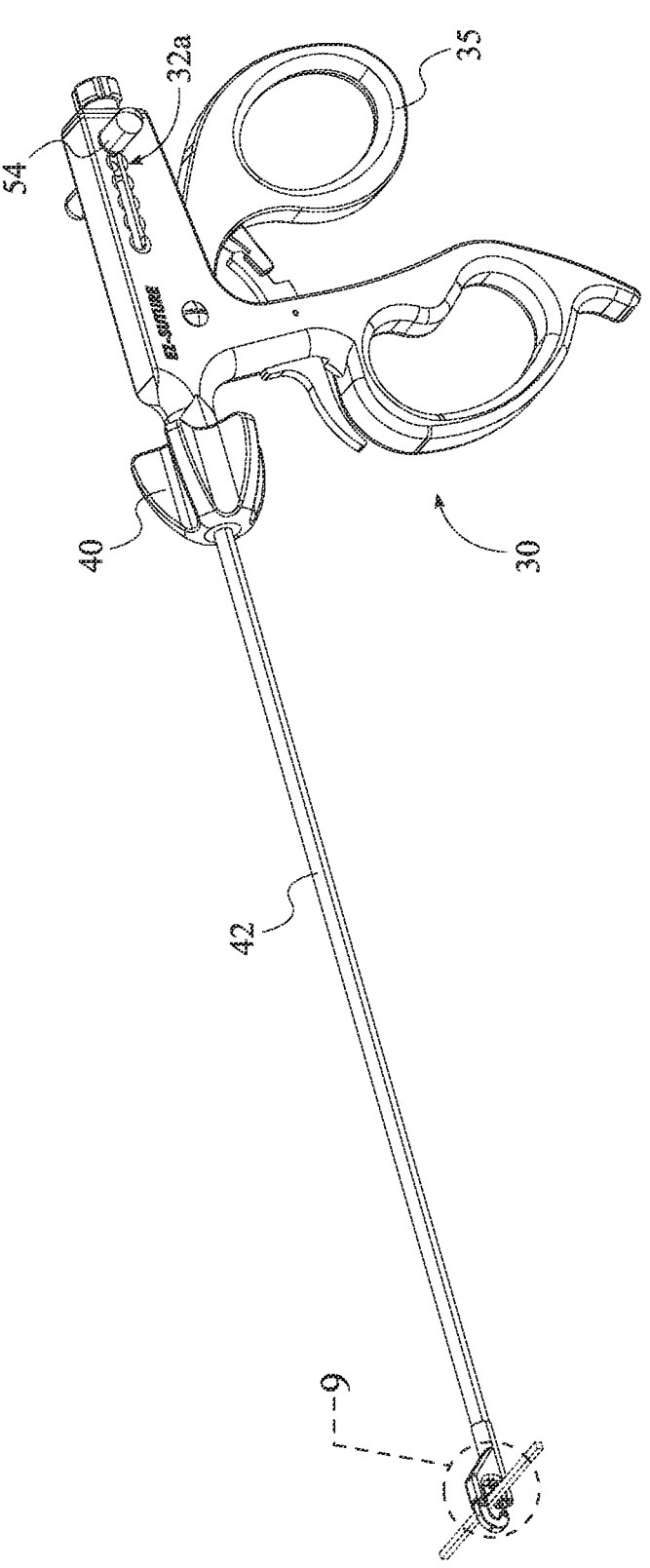
FIG. 8 is a front perspective view of the present invention, in accordance with another embodiment.

The coupler receiver 142 comprises a receiver body 143 and a receiver cavity 144, as shown in FIGS. 1, 3, and 5. The receiver body 143 is connected adjacent to the jaw body 141. The receiver cavity 144 traverses into the receiver body 143. The strand aperture 23 traverses through the receiver body 143. In the preferred embodiment of the present invention, the receiver body 143, in conjunction with the receiver cavity 144, mounts the first coupler 15 and the second coupler 16 along the first jaw 13 and the second jaw 14 of the surgical suturing device 1. In the preferred embodiment of the present invention, the first coupler 15 and the second coupler 16 each is a snap-rivet coupler 26, as shown in FIG. 6. In the preferred embodiment of the present invention, the first coupler 15 and the second coupler 16 each is a ball and socket coupler 25, as shown in FIG. 6. In various embodiments of the present invention, the first coupler 15 and the second coupler 16 may take the form of any other suitable type of coupling implement, such as, but not limited to barb connectors, tabs, adhesives, welding agents, or any other suitable coupling implement. In reference to FIG. 6, the first coupler comprises a coupler fastener 163. The second coupler comprises a coupler cavity 162. The coupler fastener 163 is positioned adjacent to the strand receiver of the first coupler. The coupler cavity 162 is positioned adjacent to the strand receiver of the second coupler. The coupler fastener 163 is connected to the coupler cavity 162 when the coupler fastener 163 of the first coupler and the coupler cavity 162 of the second coupler are pressed together when the first jaw and the second jaw are in a closed configuration. The coupler fastener 163 serves as the male connection implement of the first coupler and the coupler cavity 162 serves as the female connection implement of the second coupler.

In the preferred embodiment of the present invention, the surgical suturing device 1 comprises a suture channel 24, as shown in FIGS. 1-5. The suture channel 24 traverses through the shaft 21. The suture channel 24 allows the user to replace the spent suture cord 2 with a pre-knotted suture along the shaft 21 portion of the surgical suturing device 1 ready for the next suture operation.

Figure 10:
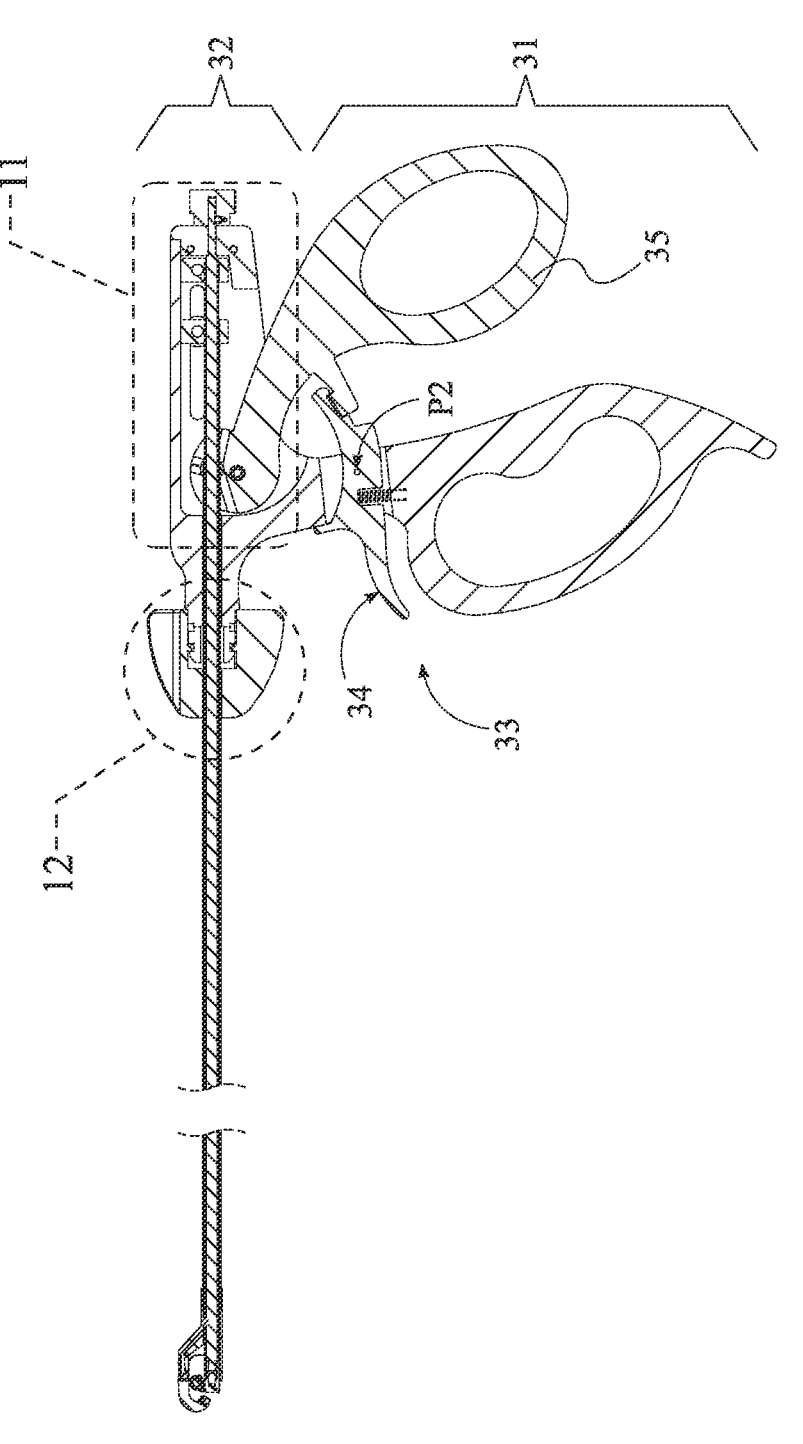
FIG. 10 is a front cutaway view of the present invention, in accordance with another embodiment.
Figure 11:
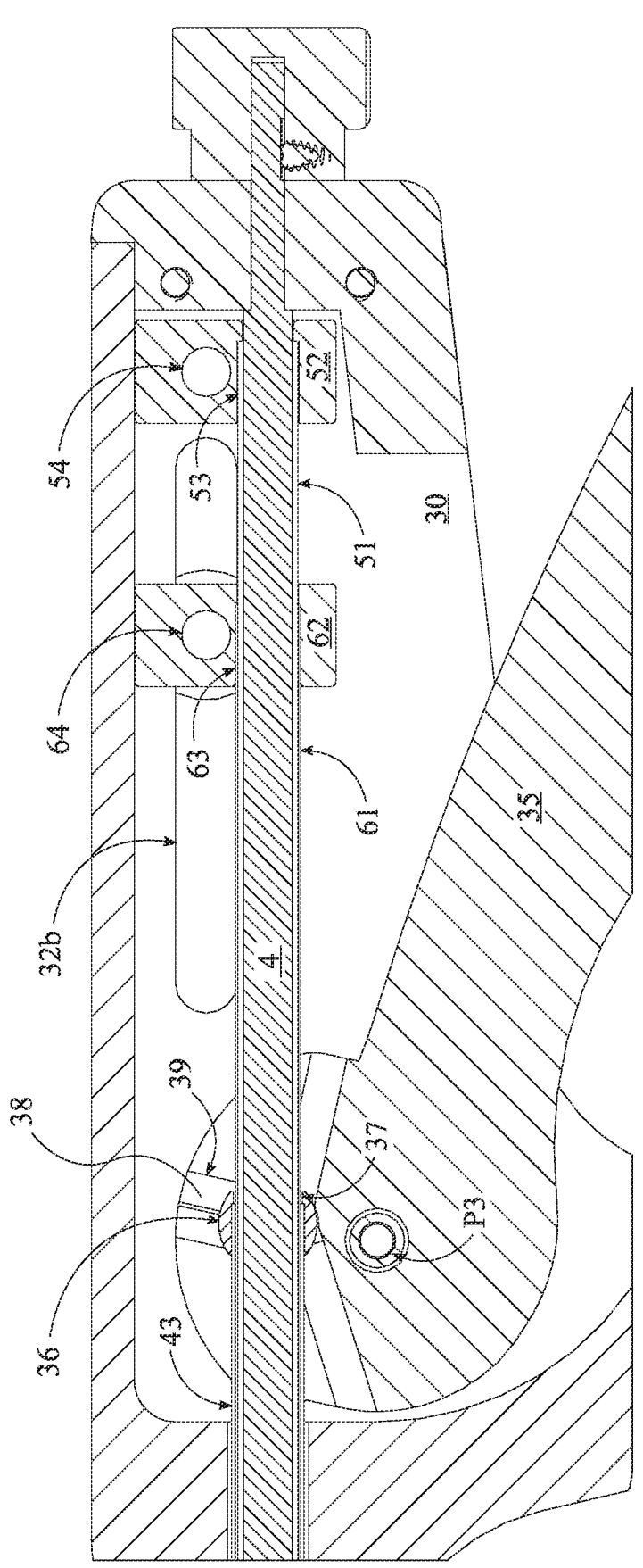
FIG. 11 is a magnified view taken from FIG. 10, showing the handle housing.
Figure 12:
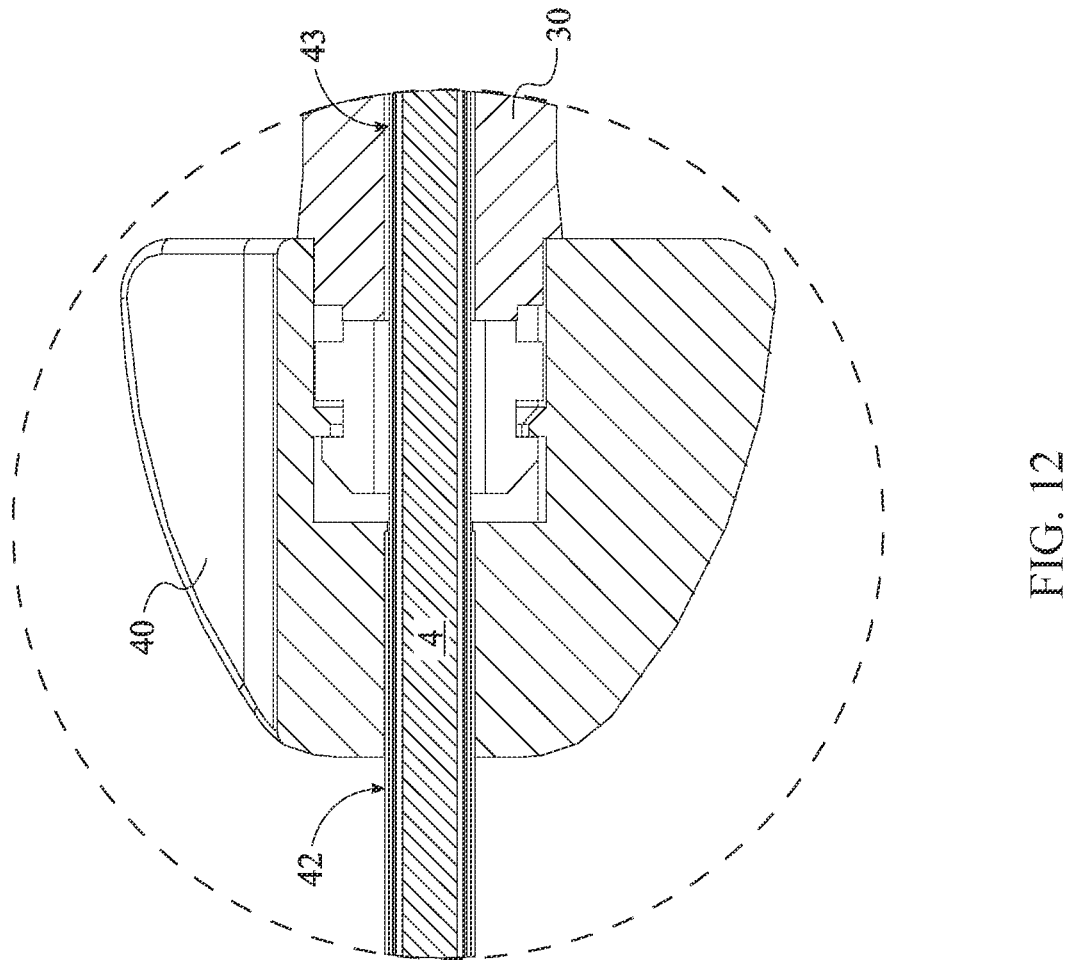
FIG. 12 is a magnified view taken from FIG. 10, showing the rotary knob.

In a second embodiment, in reference to FIGS. 7-23, the surgical suturing device 1 comprises a handle 30, a shaft 4, an outer tube 42, a clamp tube 43, a clamp end 44, a grasping mechanism 45, a pivot arm 46, a first coupler 15, and a second coupler 16. In this embodiment, the present invention can be of any shape, size, material, features, type or kind, orientation, location, quantity, components, and arrangements of components that would allow the present invention to fulfill the objectives and intents of the present invention. However, it can be preferred that the present invention be of a material that is sterile, hygienic, strong, durable, tough, light weight, easily cleanable, and/or easily manufacturable. In reference to FIGS. 10-12, the handle 30 further comprises a grip section 31 and a housing section 32, wherein the grip section 31 is positioned below the housing section 32. As seen in FIG. 11-12, both the shaft 4 and the outer tube 42 are terminally connected to the housing section 32 of the handle 30, each extending outward in the forward direction. In particular, the outer tube 42 is concentric with the shaft 4, such that the outer tube 42 surrounds the shaft 4. The clamp tube 43 is also concentric with the shaft 4, positioned between the shaft 4 and the outer tube 42. In this arrangement, the clamp tube 43 slidably engages with the outer tube 42. Furthermore, the clamp tube 43 is operatively connected to a trigger mechanism 33 of the handle 30. As will be described in further detail below, pressing the trigger 34 causes the clamp tube 43 to slide aft, which in turn, activates the pivot arm 46 to move in the closed configuration, thereby joining the first coupler 15 to the second coupler 16.

Figures 13, 14:
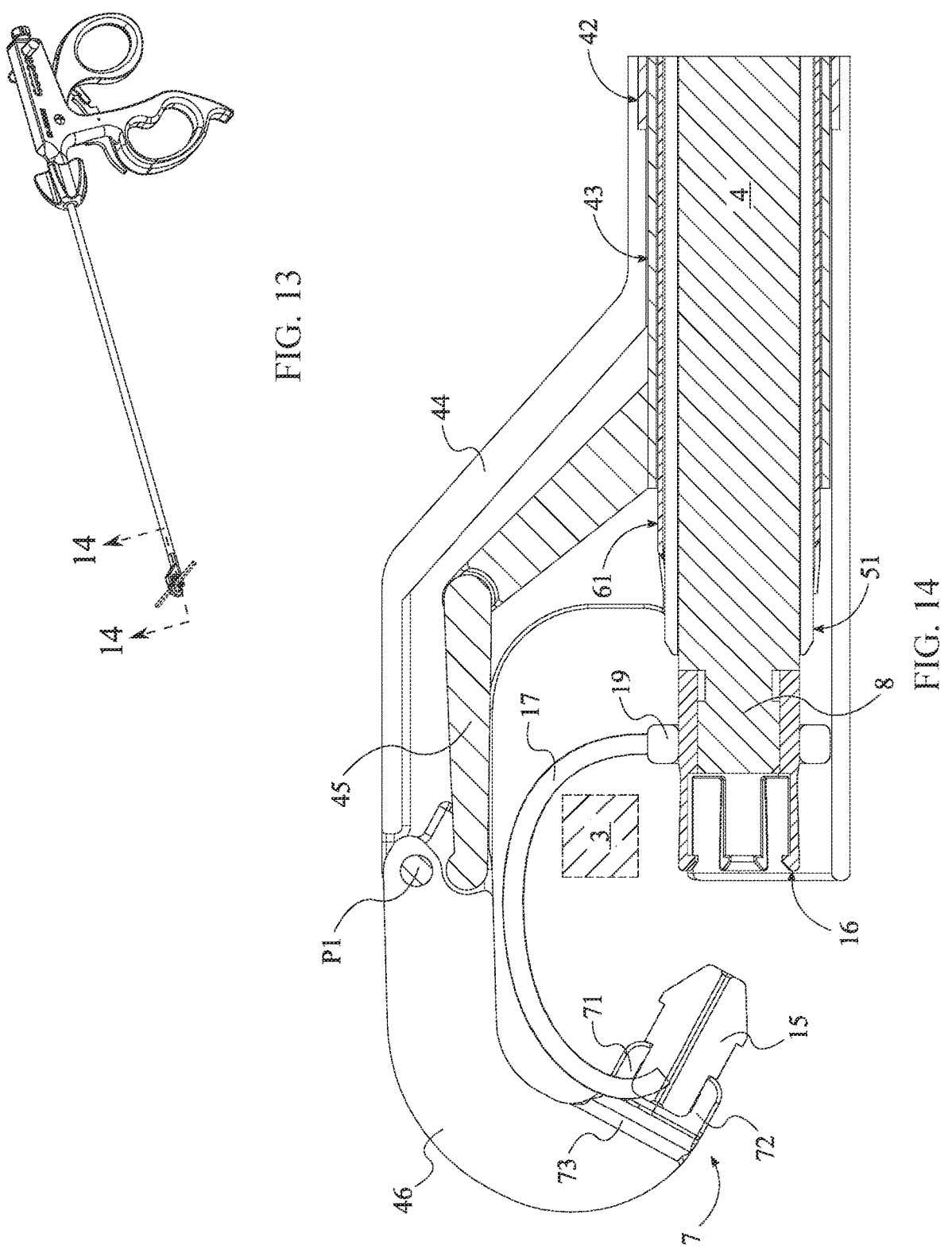
FIG. 13 is a front perspective view of the present invention, in accordance with another embodiment.
FIG. 14 is an enlarged, cross-sectional view taken along line 14-14 in FIG. 13.

Preferably, the housing section 32 of the handle 30 further comprises a rotary knob 40. As best seen in FIG. 12, the rotary knob 40 surrounds the shaft 4 and is rotatably connected to a distal end of the housing section 32. The outer tube 42 is terminally connected to the rotary knob 40. As best seen in FIG. 14, the clamp end 44 is terminally connected to a distal end of the outer tube 42. In this arrangement, the user can rotate the clamp end 44 to a desired position by twisting the rotary knob 40 clockwise or counterclockwise. Thus, the rotary knob 40 allows the user to maneuver the clamp end 44 around the suturing portion 3 without having to rotate the entire surgical suturing device 1. In other embodiments, the outer tube 42 is directly connected to the handle 30, wherein the proximal end of the outer tube 42 is terminally connected to a distal end of the handle 30.

In reference to FIG. 14, the clamp end 44 is U-shaped, which creates a sufficient gap for insertion of the suturing portion 3. The pivot arm 46 is C-shaped and is used to close the gap and secure the suture to the suturing portion 3. In particular, the pivot arm 46 is pivotally connected to a distal end of the clamp end 44, via a first pivot pin P1. The grasping mechanism 45 is housed within the clamp end 44. The grasping mechanism 45 connects the clamp tube 43 to the pivot arm 46. When using the device, the pivot arm 46 is actuated and controlled by the sliding movement of the clamp tube 43. Since the clamp tube 43 is operatively connected to the trigger mechanism 33 of the handle 30, the user can actuate and control the movement of the pivot arm 46 by pressing and releasing the trigger 34.

Continuing with the second embodiment, the handle 30 further comprises a trigger mechanism 33. As can be seen in FIGS. 10-11, the trigger mechanism 33 is configured so that when the user squeezes down on the trigger 34, the clamp tube 43 slides aft, causing the pivot arm 46 to move into a closed configuration. When the user releases the trigger 34, the clamp tube 43 slides forward, causing the pivot arm 46 to retract back into an open configuration. To perform this function, the trigger mechanism 33 comprises a spring-loaded trigger 34 and a thumb grip 35. The trigger 34 is pivotally connected to the grip section 31 of the handle 30 via a second pivot pin P2. The trigger 34 is detachably connected to the thumb grip 35, wherein the thumb grip is positioned behind the trigger 34. The thumb grip 35 extends upward into the housing section 32 and is pivotally connected to the housing section 32 via a third pivot pin P3. The third pivot pin P3 extends through the housing section 32 and is positioned below the shaft 4. In this arrangement, pressing down on the trigger 34 causes the thumb grip 35 to rotate downward in a clockwise direction.

Continuing with the trigger mechanism 33, the thumb grip 35 is operatively connected to the clamp tube 43 using a ball and track arrangement. As seen in FIG. 11, a ball follower 36 is terminally connected to the proximal end of the clamp tube 43. An aperture 37 is disposed on the ball follower 36, which allows the ball follower 36 to slidably engage with the shaft 4. The thumb grip 35 is notched at the top end to clear the shaft 4 passing through. A groove 38 (i.e., linear track) is disposed on the top end of the thumb grip 35, configured for receiving the ball follower 36. Thus, the ball follower 36 slidably engages with both the shaft 4 and the groove 38 of the thumb grip 35. As the thumb grip 35 rotates about the third pivot pin P3, a plurality of inner edges 39 on the groove 38 engage with the ball follower 36, thereby causing the ball follower 36 to slide along the shaft 4 in the aft direction. Thus, the rotational motion of the thumb grip 35 corresponds with a sliding motion of the ball follower 36. In turn, the clamp tube 43 also slides in the aft direction, which then activates the pivot arm 46 to move into the closed position. It is understood that other forms of trigger mechanisms can be utilized without departing from the scope of the present invention, including but not limited to fork joints, pushrods, and rack and pinion gears.

Continuing with the second embodiment, the pivot arm 46 further comprises a first coupler receiver 7. As seen in FIG. 14, the first coupler receiver 7 is terminally connected to a distal end of the pivot arm 46. The first coupler receiver 7 mounts the first coupler 15 to the pivot arm 46, such that the first coupler 15 is removably positioned within the first coupler receiver 7. To mount the second coupler 16, the shaft 4 further comprises a second coupler receiver 8. The second coupler receiver 8 is terminally connected to a distal end of the shaft 4. The second coupler receiver 8 is shaped to receive the second coupler 16. The second coupler receiver 8 mounts the second coupler 16 to the shaft 4, such that the second coupler 16 is removably positioned within the second coupler receiver 8.

Continuing with the second embodiment, the first coupler receiver 7 further comprises a receiver body 71, a receiver cavity 72, and a strand aperture 73. As can be seen in FIG. 14, the receiver body 71 is connected adjacent to the distal end of the pivot arm 46. The receiver cavity 72 traverses into the receiver body 71, wherein the receiver cavity 72 is shaped to receive the first coupler 15. The strand aperture 73 traverses through the receiver body 71, thereby providing an opening for the first strand 17 to pass through. In this arrangement, the receiver body 71, in conjunction with the receiver cavity 72, mounts the first coupler 15 to the pivot arm 46 of the surgical suturing device 1.

Figures 15, 16:
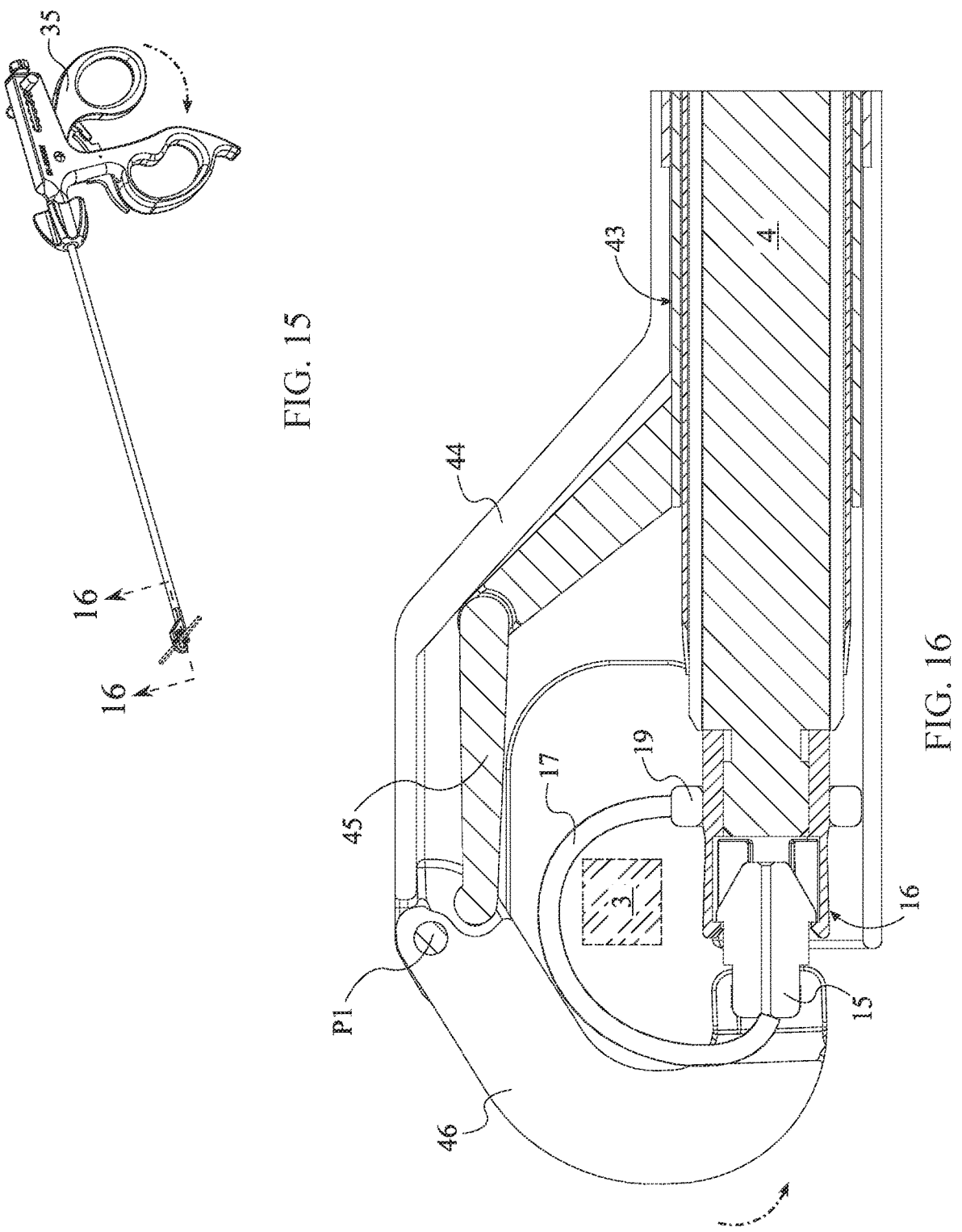
FIG. 15 is a front perspective view of the present invention, in accordance with another embodiment, showing the trigger pressed.
FIG. 16 is an enlarged, cross-sectional view taken along line 16-16 in FIG. 15.
Figures 17, 18:
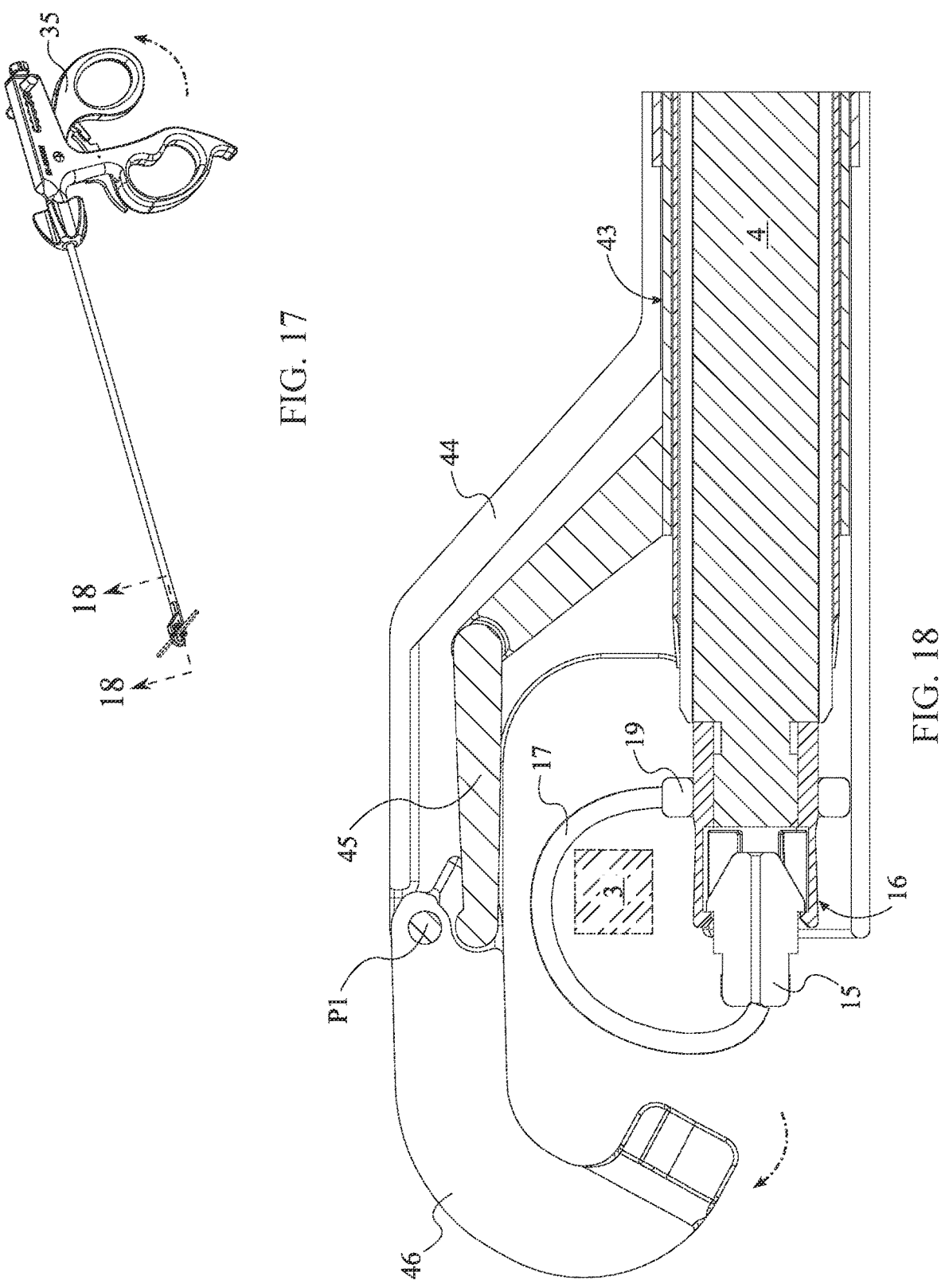
FIG. 17 is a front perspective view of the present invention, in accordance with another embodiment, showing the trigger released.
FIG. 18 is an enlarged, cross-sectional view taken along line 18-18 in FIG. 17.
Figures 19, 20:
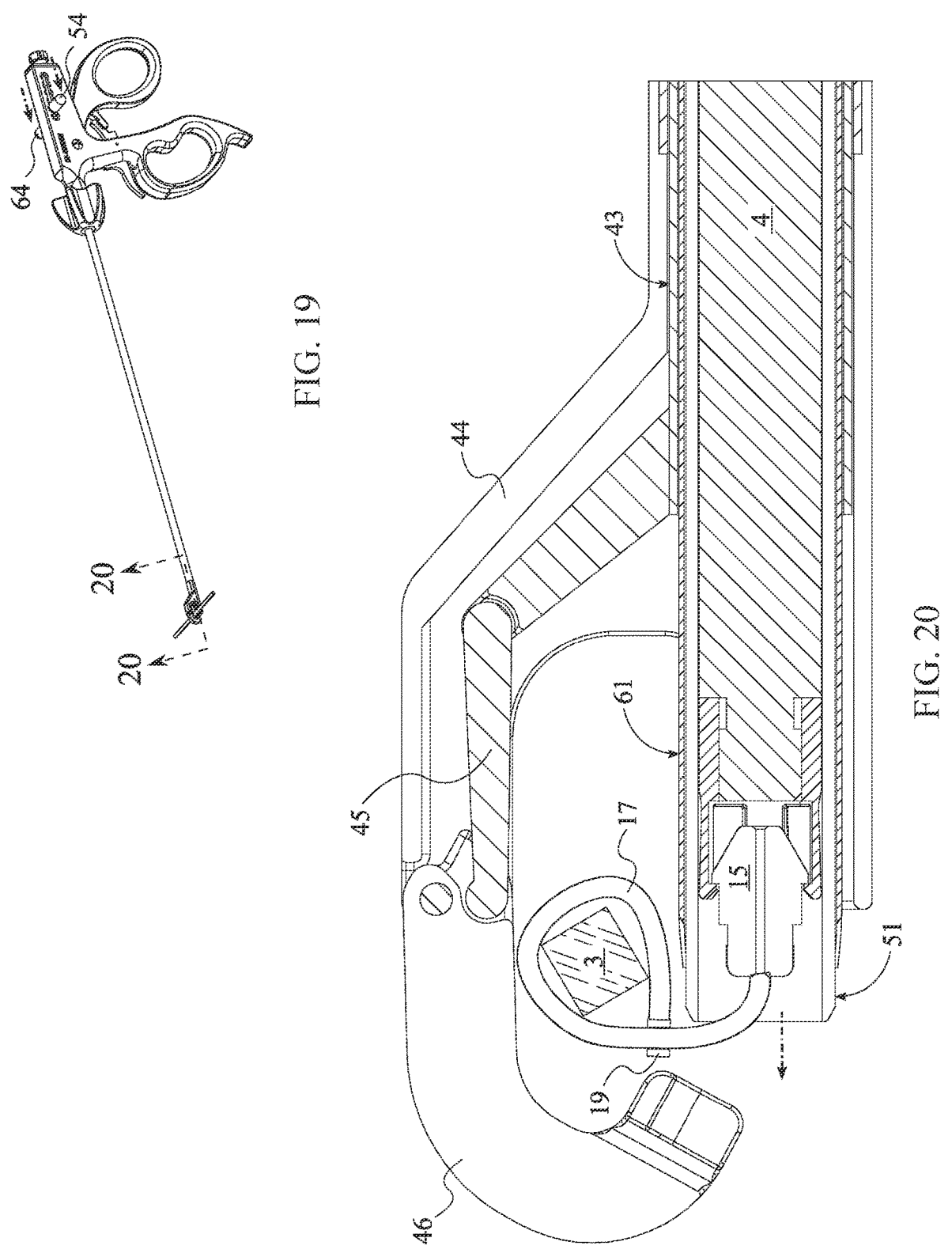
FIG. 19 is a front perspective view of the present invention, in accordance with another embodiment, showing the knot pusher activated.
FIG. 20 is an enlarged, cross-sectional view taken along line 20-20 in FIG. 19.

Continuing with the second embodiment, the suture cord 2 further comprises a first strand 17 and a suture knot 19. As best seen in FIG. 14, the first strand 17 is connected to the strand receiver 161 of the first coupler 15. The suture knot 19 is operatively connected to the first strand 17. The suture knot 19 is detachably connected to the second coupler 16. More specifically, the suture knot 19 is perimetrically fitted around the second coupler. The first strand 17 serves as a segment of the suture cord 2 that will form a closed loop in conjunction with the suture knot 19. When activating the pivot arm 46, as illustrated in FIG. 16, the first coupler 15 connects to the second coupler 16. As the pivot arm 46 retracts back to the open position, as illustrated in FIG. 18, the first coupler 15 detaches from the pivot arm 46 and remains attached to the second coupler 16. Next, as illustrated in FIG. 20, the suture knot 19 can be pushed forward and slide through the first coupler 15 and through the first strand 17, thereby forming a closed loop around the suturing portion 3. The suture knot 19 may take the form of any suitable adjustment element used to tighten the newly formed closed loop along a suturing portion 3.

Figure 23:
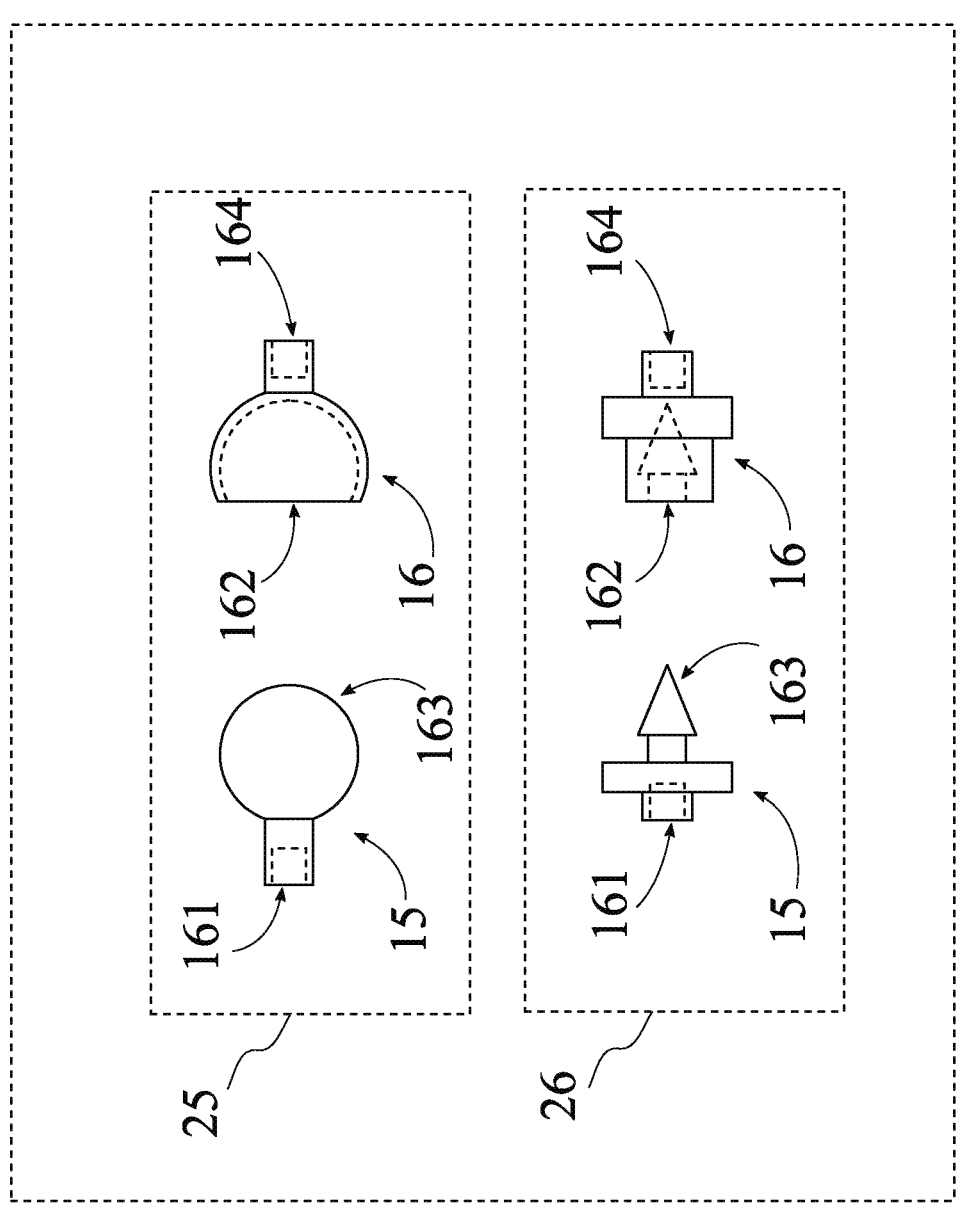
FIG. 23 is a diagram view of a ball and socket coupler and a snap rivet coupler, in accordance with another embodiment.

In reference to FIG. 23, continuing with the second embodiment, the first coupler and the second coupler 16 each is a snap-rivet coupler 26. Alternatively, the first coupler 15 and the second coupler 16 can each be a ball and socket coupler 25. In various embodiments of the present invention, the first coupler 15 and the second coupler 16 may take the form of any other suitable type of coupling implement, such as, but not limited to barb connectors, tabs, adhesives, welding agents, or any other suitable coupling implement. The first coupler 15 comprises a strand receiver 161 and a coupler fastener 163. The strand receiver 161 traverses into the first coupler 15. The coupler fastener 163 is positioned adjacent to the strand receiver of the first coupler. The second coupler 16 comprises a shaft receiver 164 and a coupler cavity 162. The shaft receiver 164 traverses into the second coupler. The coupler cavity 162 is positioned adjacent to the shaft receiver 164 of the second coupler. The coupler fastener 163 is connected to the coupler cavity 162 when the coupler fastener 163 of the first coupler and the coupler cavity 162 of the second coupler are pressed together when the pivot arm 46 is in a closed configuration. The coupler fastener 163 serves as the male connection implement of the first coupler and the coupler cavity 162 serves as the female connection implement of the second coupler.

Figure 9:
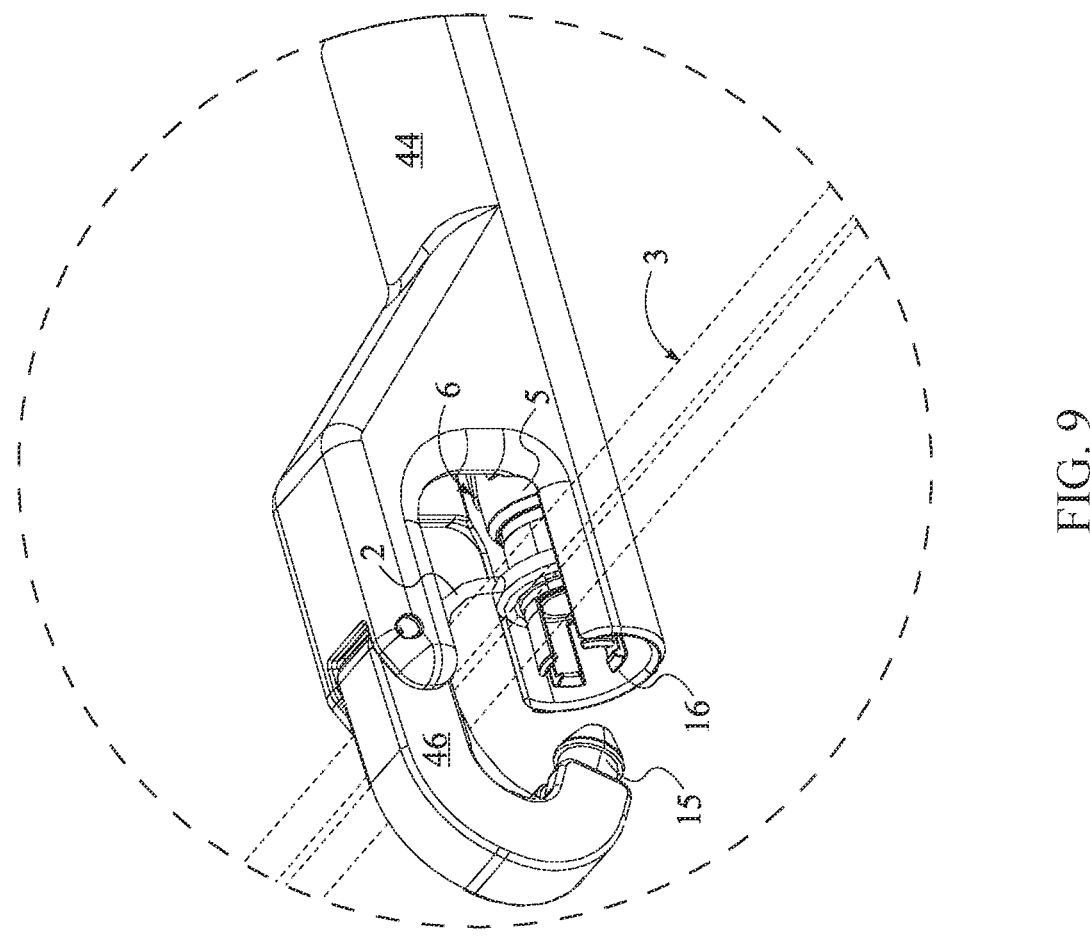
FIG. 9 is a magnified view taken from FIG. 8, showing the pivot arm.

As can be seen in FIG. 9, continuing with the second embodiment, the surgical suturing device 1 further comprises a knot pusher 5. After engaging the pivot arm 46 and securing the first coupler 15 to the second coupler 16, the user can then activate the knot pusher 5 to push the suture knot 19 off the second coupler 16 and pressed up against the suturing portion 3, as illustrated in FIG. 19-20. In effect, the knot pusher 5 removes the excess slack in the newly formed closed loop around the suturing portion 3.

To perform this function, the knot pusher 5 further comprises a pusher tube 51, a pusher block 52, and a pusher knob 54. As seen in FIG. 11, the pusher tube 51 surrounds the shaft 4, such that the pusher tube 51 is positioned between the shaft 4 and the clamp tube 43. Thus, the pusher tube 51 slidably engages with the shaft 4. A proximal end of the pusher tube 51 is terminally connected to the pusher block 52. The pusher block 52 is positioned within the housing section 32 of the handle 30. The pusher block 52 slidably engages with the shaft 4 via an aperture 53 axially disposed on the pusher block 52. To slide the pusher tube 51 and the pusher block 52 forward and aft, the pusher knob 54 is connected to a side surface of the pusher block 52, extending laterally outward. For disassembly and maintenance, preferably, the pusher knob 54 is detachably connected to the pusher block 52 via a threaded fastening system. In particular, the pusher knob 54 has a threaded end. The threaded end is configured to be inserted and fastened into a corresponding threaded opening disposed on the side surface of the pusher block 52. In other embodiments, the pusher knob 54 is terminally connected to the pusher block 52. To slide the pusher knob 54 across the handle 30, the housing section 32 further comprises a first slotted cutout 32a. The first slotted cutout 32a is disposed on a side surface of the housing section 32. The shape and positioning of the first slotted cutout 32a is delineated by the pusher knob 54 extending through. In this arrangement, moving the pusher knob 54 forward along the first slotted cutout 32a forces the pusher tube 51 to also move forward, thereby pushing the suture knot 19 up to the suturing portion 3. Pulling the pusher knob 54 in the aft direction forces the pusher tube 51 to retract back to the retracted position.

Figures 21, 22:
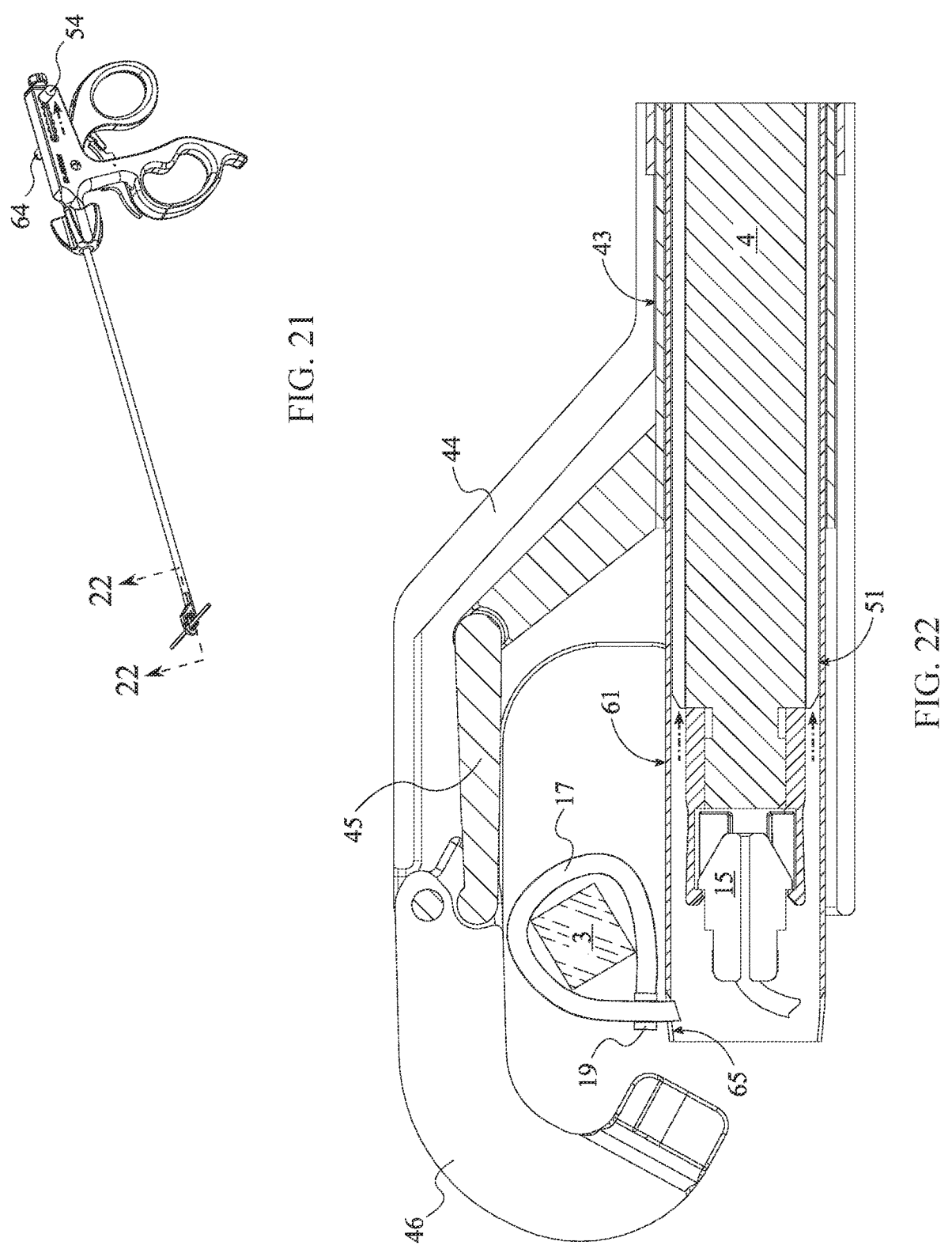
FIG. 21 is a front perspective view of the present invention, in accordance with another embodiment, showing the cutter activated.
FIG. 22 is an enlarged, cross-sectional view taken along line 22-22 in FIG. 21.

As can be seen in FIG. 9, continuing with the second embodiment, the surgical suturing device 1 further comprises a cutter 6. After activating the knot pusher 5 to push the suture knot 19 up against the suturing portion 3, the user can then activate the cutter 6 to cut the excess suture cord 2. The cutter 6 is arranged such that both the cutter tube 61 and the pusher tube 51 slide together in unison as the pusher knob 54 is being pushed forward to the extended position, as illustrated in FIGS. 19-20. While moving into the extended position, the tip 65 of the cutter tube 61 remains offset and aft of the tip of the pusher tube 51. Thus, the pusher tube 51 also functions as a protective sheath to cover the tip 65 of the cutter tube 61 when activating the knot pusher 5. Once tightened, the user can then slide the pusher tube 51 back to the retracted position while keeping the cutter tube 61 in the extended position, as illustrated in FIGS. 21-22. In turn, the tip 65 of the cutter tube 61 is now exposed to the suture cord 2, allowing the user to cut the excess suture cord 2. Preferably, the tip 65 of the cutter tube 61 is in the form of a V-shaped notch. Thus, the user can place the suture cord 2 within the V-shaped notch and cut the suture cord 2 thereafter. The suture cord 2 is then detached from the first coupler 15, which allows the user to safely remove the surgical suturing device 1 away from the newly formed closed loop.

To perform this function, the cutter 6 further comprises a cutter tube 61, a cutter block 62, and a cutter knob 64. As seen in FIG. 11, the cutter tube 61 surrounds the pusher tube 51, such that the cutter tube 61 is positioned between the pusher tube 51 and the clamp tube 43. Thus, the cutter tube 61 slidably engages with the pusher tube 51. A proximal end of the cutter tube 61 is terminally connected to the cutter block 62. The cutter block 62 is positioned within the housing section 32 of the handle 30. The cutter block 62 slidably engages with the pusher tube 51 via an aperture 63 axially disposed on the cutter block 62. Furthermore, the cutter block 62 is positioned forward of the pusher block 52. This arrangement allows the user to extend both the pusher tube 51 and the cutter tube 61 together by sliding the pusher knob 54 forward. Once extended, the user can then independently retract the pusher tube 51 while keeping the cutter tube 61 in the extended position. To slide the cutter tube 61 and the cutter block 62 forward and aft, the cutter knob 64 is connected to a side surface of the cutter block 62, extending laterally outward. For disassembly and maintenance, preferably, the cutter knob 64 is detachably connected to the cutter block 62 via a threaded fastening system. In particular, the cutter knob 64 has a threaded end. The threaded end is configured to be inserted and fastened into a corresponding threaded opening disposed on the side surface of the cutter block 62. In other embodiments, the cutter knob 64 is terminally connected to the cutter block 62. To slide the cutter knob 64 across the handle 30, the housing section 32 further comprises a second slotted cutout 32*b*. The second slotted cutout 32*b* is disposed on a side surface of the housing section 32, opposite the first slotted cutout 32*a*. The shape and positioning of the second slotted cutout 32*b* is delineated by the cutter knob 64 extending through. In this arrangement, moving the cutter knob 64 forward along the second slotted cutout 32*b* forces the cutter tube 61 to also move forward, thereby positioning the tip 65 of the cutter tube 61 near the suture cord 2. After cutting the suture cord 2, the user can slide the cutter tube 61 back to the retracted position by pulling the cutter knob 64 in the aft direction.

Although the invention has been explained in relation to its preferred embodiment, it is to be understood that many other possible modifications and variations can be made without departing from the spirit and scope of the invention as hereinafter claimed.

What is claimed is:

1. A surgical suturing device comprising:
 a handle;
 a shaft;
 an outer tube;
 a clamp tube;

a clamp end;
 a pivot arm;
 a grasping mechanism;
 a first coupler;
 a second coupler;
 the handle further comprising a housing section and a grip section;
 the shaft being terminally connected to the housing section;
 the outer tube being terminally connected to the housing section;
 the outer tube being concentric with the shaft;
 the clamp tube being concentric with the shaft;
 the clamp tube being operatively connected to the handle;
 the clamp tube slidably engaging with the outer tube;
 the clamp end being terminally connected to a distal end of the outer tube;
 the pivot arm being pivotally connected to a distal end of the clamp end;
 the pivot arm being operatively connected the clamp tube via the grasping mechanism;
 the grasping mechanism connecting the clamp tube to the pivot arm;
 the pivot arm further comprising a first coupler receiver;
 the first coupler receiver being positioned on a distal end of the pivot arm;
 the first coupler being removably positioned within the first coupler receiver;
 the shaft further comprising a second coupler receiver;
 the second coupler receiver being positioned on a distal end of the shaft;
 the second coupler being removably positioned within the second coupler receiver;
 the first coupler comprising a coupler fastener;
 the second coupler comprising a coupler cavity; and
 the pivot arm capable of connecting the coupler fastener of the first coupler to the coupler cavity of the second coupler in a closed configuration.

2. The surgical suturing device as claimed in claim 1 comprising:
 the handle further comprising a trigger mechanism;
 the trigger mechanism comprising a trigger, a thumb grip, and a ball follower;
 the trigger being pivotally connected to the grip section of the handle;
 the trigger being connected to the thumb grip;
 the thumb grip being pivotally connected to the housing section;
 the thumb grip being operatively connected to the clamp tube via the ball follower;
 the ball follower being terminally connected to a proximal end of the clamp tube;
 the ball follower being adapted to slidably engage with the shaft;
 a groove being disposed on top of the thumb grip; and
 the ball follower slidably engaging with the groove of the thumb grip.

3. The surgical suturing device as claimed in claim 1 comprising:
 a suture knot;
 a first strand;
 the first coupler further comprising a strand receiver;
 the strand receiver being positioned adjacent to the coupler fastener;
 the first strand being connected to the strand receiver;
 the second coupler further comprising a shaft receiver;

the shaft receiver being positioned adjacent to the coupler cavity;

the shaft being connected to the shaft receiver;

the suture knot being perimetrically fitted to the second coupler; and the suture knot being operatively connected to the first strand.

4. The surgical suturing device as claimed in claim 3 comprising:

a knot pusher;

the knot pusher comprising a pusher tube;

the pusher tube being concentric with the shaft;

the pusher tube slidably engaging with the shaft; and the pusher tube capable of pushing the suture knot through the first strand and tightening a loop formed thereby.

5. The surgical suturing device as claimed in claim 4 comprising:

the knot pusher further comprising a pusher block and a pusher knob;

the pusher block being terminally connected to a proximal end of the pusher tube;

the pusher block being adapted to slidably engage with the shaft;

the pusher knob being laterally connected to the pusher block;

the housing section comprising a first slotted cutout; and the pusher knob extending outward through the first slotted cutout.

6. The surgical suturing device as claimed in claim 4 comprising:

a cutter;

the cutter comprising a cutter tube;

the cutter tube being concentric with the shaft;

the cutter tube slidably engaging with the pusher tube; and the cutter tube capable of cutting the first strand after activating the knot pusher.

7. The surgical suturing device as claimed in claim 6 comprising:

the cutter further comprising a cutter block and a cutter knob;

the cutter block being terminally connected to a proximal end of the cutter tube;

the cutter block being adapted to slidably engage with the pusher tube;

the cutter knob being laterally connected to the cutter block;

the housing section comprising a second slotted cutout; and the cutter knob extending outward through the second slotted cutout.

8. The surgical suturing device as claimed in claim 1 comprising:

the housing section further comprising a rotary knob;

the rotary knob being concentric with the shaft;

the rotary knob being rotatably connected to a distal end of the housing section; and the outer tube being terminally connected to the rotary knob.

9. The surgical suturing device as claimed in claim 1 comprising:

the first coupler receiver comprising a receiver body, a receiver cavity, and a strand aperture;

the receiver cavity traversing into the receiver body;

the receiver cavity being adapted to fit the first coupler; and the strand aperture traversing through the receiver body.

10. A surgical suturing device comprising:

a handle;

a shaft;

an outer tube;

a clamp tube;

a clamp end;

a pivot arm;

a grasping mechanism;

a first coupler;

a second coupler;

a suture knot;

a first strand;

the handle further comprising a housing section and a grip section;

the shaft being terminally connected to the housing section;

the outer tube being terminally connected to the housing section;

the outer tube being concentric with the shaft;

the clamp tube being concentric with the shaft;

the clamp tube being operatively connected to the handle;

the clamp tube slidably engaging with the outer tube;

the clamp end being terminally connected to a distal end of the outer tube;

the pivot arm being pivotally connected to a distal end of the clamp end;

the pivot arm being operatively connected the clamp tube via the grasping mechanism;

the grasping mechanism connecting the clamp tube to the pivot arm;

the pivot arm further comprising a first coupler receiver;

the first coupler receiver being positioned on a distal end of the pivot arm;

the first coupler being removably positioned within the first coupler receiver;

the shaft further comprising a second coupler receiver;

the second coupler receiver being positioned on a distal end of the shaft;

the second coupler being removably positioned within the second coupler receiver;

the suture knot being perimetrically fitted to the second coupler;

the suture knot being operatively connected to the first strand;

the first coupler comprising a coupler fastener and a strand receiver;

the coupler fastener being positioned adjacent to the strand receiver;

the first strand being connected to the strand receiver;

the second coupler comprising a coupler cavity and a shaft receiver;

the coupler cavity being positioned adjacent to the shaft receiver;

the shaft being connected to the shaft receiver; and the pivot arm capable of connecting the coupler fastener of the first coupler to the coupler cavity of the second coupler in a closed configuration.

11. The surgical suturing device as claimed in claim 10 comprising:

the handle further comprising a trigger mechanism;

the trigger mechanism comprising a trigger, a thumb grip, and a ball follower;

the trigger being pivotally connected to the grip section of the handle;

the trigger being connected to the thumb grip;

the thumb grip being pivotally connected to the housing section;

the thumb grip being operatively connected to the clamp tube via the ball follower;

the ball follower being terminally connected to a proximal end of the clamp tube;

the ball follower being adapted to slidably engage with the shaft;

a groove being disposed on top of the thumb grip; and the ball follower slidably engaging with the groove of the thumb grip.

12. The surgical suturing device as claimed in claim 10 comprising:

a knot pusher;

the knot pusher comprising a pusher tube, a pusher block, and a pusher knob;

the pusher tube being concentric with the shaft;

the pusher tube slidably engaging with the shaft;

the pusher block being terminally connected to a proximal end of the pusher tube;

the pusher block being adapted to slidably engage with the shaft;

the pusher knob being laterally connected to the pusher block;

the housing section comprising a first slotted cutout;

the pusher knob extending outward through the first slotted cutout; and the pusher tube capable of pushing the suture knot through the first strand and tightening a loop formed thereby.

13. The surgical suturing device as claimed in claim 12 comprising:

a cutter;

the cutter comprising a cutter tube, a cutter block, and a cutter knob;

the cutter tube being concentric with the shaft;

the cutter tube slidably engaging with the pusher tube;

the cutter block being terminally connected to a proximal end of the cutter tube;

the cutter block being adapted to slidably engage with the pusher tube;

the cutter knob being laterally connected to the cutter block;

the housing section comprising a second slotted cutout;

the cutter knob extending outward through the second slotted cutout; and the cutter tube capable of cutting the first strand after activating the knot pusher.

14. The surgical suturing device as claimed in claim 10 comprising:

the housing section further comprising a rotary knob;

the rotary knob being concentric with the shaft;

the rotary knob being rotatably connected to a distal end of the housing section; and the outer tube being terminally connected to the rotary knob.

15. The surgical suturing device as claimed in claim 10 comprising:

the first coupler receiver comprising a receiver body, a receiver cavity, and a strand aperture;

the receiver cavity traversing into the receiver body;

the receiver cavity being adapted to fit the first coupler; and the strand aperture traversing through the receiver body.

16. A surgical suturing device comprising:

a handle;

a shaft;

an outer tube;

a clamp tube;

a clamp end;

a pivot arm;

a grasping mechanism;

a first coupler;

a second coupler;

a suture knot;

a first strand;

the handle further comprising a housing section and a grip section;

the shaft being terminally connected to the housing section;

the outer tube being terminally connected to the housing section;

the outer tube being concentric with the shaft;

the clamp tube being concentric with the shaft;

the clamp tube being operatively connected to the handle;

the clamp tube slidably engaging with the outer tube;

the clamp end being terminally connected to a distal end of the outer tube;

the pivot arm being pivotally connected to a distal end of the clamp end;

the pivot arm being operatively connected the clamp tube via the grasping mechanism;

the grasping mechanism connecting the clamp tube to the pivot arm;

the pivot arm further comprising a first coupler receiver;

the first coupler receiver being positioned on a distal end of the pivot arm;

the first coupler receiver further comprising a receiver body, a receiver cavity, and a strand aperture;

the receiver cavity traversing into the receiver body;

the receiver cavity being adapted to fit the first coupler;

the strand aperture traversing through the receiver body;

the first coupler being removably positioned within the first coupler receiver;

the shaft further comprising a second coupler receiver;

the second coupler receiver being positioned on a distal end of the shaft;

the second coupler being removably positioned within the second coupler receiver;

the suture knot being perimetrically fitted to the second coupler;

the suture knot being operatively connected to the first strand;

the first coupler comprising a coupler fastener and a strand receiver;

the coupler fastener being positioned adjacent to the strand receiver;

the first strand being connected to the strand receiver;

the second coupler comprising a coupler cavity and a shaft receiver;

the coupler cavity being positioned adjacent to the shaft receiver;

the shaft being connected to the shaft receiver; and the pivot arm capable of connecting the coupler fastener of the first coupler to the coupler cavity of the second coupler in a closed configuration.

17. The surgical suturing device as claimed in claim 16 comprising:

the handle further comprising a trigger mechanism;

the trigger mechanism comprising a trigger, a thumb grip, and a ball follower;

the trigger being pivotally connected to the grip section of the handle;

the trigger being connected to the thumb grip;

the thumb grip being pivotally connected to the housing section;

the thumb grip being operatively connected to the clamp tube via the ball follower;

the ball follower being terminally connected to a proximal end of the clamp tube;

the ball follower being adapted to slidably engage with the shaft;

a groove being disposed on top of the thumb grip; and the ball follower slidably engaging with the groove of the thumb grip.

18. The surgical suturing device as claimed in claim 16 comprising:

a knot pusher;

the knot pusher comprising a pusher tube, a pusher block, and a pusher knob;

the pusher tube being concentric with the shaft;

the pusher tube slidably engaging with the shaft;

the pusher block being terminally connected to a proximal end of the pusher tube;

the pusher block being adapted to slidably engage with the shaft;

the pusher knob being laterally connected to the pusher block;

the housing section comprising a first slotted cutout;

the pusher knob extending outward through the first slotted cutout; and the pusher tube capable of pushing the suture knot through the first strand and tightening a loop formed thereby.

19. The surgical suturing device as claimed in claim 18 comprising:

a cutter;

the cutter comprising a cutter tube, a cutter block, and a cutter knob;

the cutter tube being concentric with the shaft;

the cutter tube slidably engaging with the pusher tube;

the cutter block being terminally connected to a proximal end of the cutter tube;

the cutter block being adapted to slidably engage with the pusher tube;

the cutter knob being laterally connected to the cutter block;

the housing section comprising a second slotted cutout;

the cutter knob extending outward through the second slotted cutout; and the cutter tube capable of cutting the first strand after activating the knot pusher.

20. The surgical suturing device as claimed in claim 16 comprising:

the housing section further comprising a rotary knob;

the rotary knob being concentric with the shaft;

the rotary knob being rotatably connected to a distal end of the housing section; and the outer tube being terminally connected to the rotary knob.

* * * * *